(12) United States Patent
Stabile et al.

(10) Patent No.: US 8,765,962 B1
(45) Date of Patent: *Jul. 1, 2014

(54) VERY EFFICIENT PROCESS FOR PREPARING AN INTERMEDIATE OF ETORICOXIB

(71) Applicant: F.I.S.—Fabbrica Italiana Sintetici S.p.A., Alte di Montecchio Maggiore-Vicenza (IT)

(72) Inventors: Paolo Stabile, Verona (IT); Marco Galvagni, Verona (IT)

(73) Assignee: F.I.S.—Fabrica Italiana Sintetici S.p.A., Alte di Montecchio Maggiore-Vicenza (IT)

( * ) Notice: Subject to any disclaimer, the term of this patent is extended or adjusted under 35 U.S.C. 154(b) by 0 days.

This patent is subject to a terminal disclaimer.

(21) Appl. No.: 13/924,094

(22) Filed: Jun. 21, 2013

(30) Foreign Application Priority Data

Jan. 22, 2013 (IT) ................ VI2013A0014

(51) Int. Cl.
*C07D 213/50* (2006.01)

(52) U.S. Cl.
CPC .................................. *C07D 213/50* (2013.01)
USPC ............................................. 546/315

(58) Field of Classification Search
CPC ...................................... C07D 213/50
See application file for complete search history.

(56) References Cited

FOREIGN PATENT DOCUMENTS

EP 2497767 9/2012
WO WO 03/002118 A1 * 1/2003

* cited by examiner

*Primary Examiner* — Zinna Nortington Davis
(74) *Attorney, Agent, or Firm* — Lucas & Mercanti, LLP

(57) ABSTRACT

The present invention relates to an efficient process for preparing 1-(6-methylpyridin-3-yl)-2-[4-(methylsulfonyl)phenyl]ethanone, an intermediate of the synthesis of Etoricoxib. Water is employed as reaction medium.

11 Claims, No Drawings

VERY EFFICIENT PROCESS FOR PREPARING AN INTERMEDIATE OF ETORICOXIB

CROSS-REFERENCE TO RELATED APPLICATIONS

This Patent Application claims priority to and the benefit of Italian Patent Application No. VI2013A000014 filed on Jan. 22, 2013, the contents of which are incorporated herein by reference.

TECHNICAL FIELD

The object of the present invention is a very efficient process for preparing 1-(6-methylpyridin-3-yl)-2-[4-(methylsulfonyl)phenyl]ethanone, an intermediate of the synthesis of Etoricoxib, which is an active pharmaceutical ingredient, COX-2 inhibitor.

BACKGROUND ART 1-(6-methylpyridin-3-yl)-2-[4-(methylsulfonyl)phenyl] ethanone of formula (I):

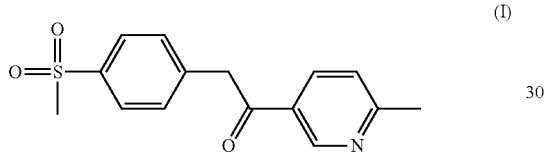

(I)

having CAS RN 221615-75-4 is an important intermediate for the synthesis of Etoricoxib, which is an active pharmaceutical ingredient belonging to the class of COX-2 inhibitors and has been on the market since 2002 with the trade name Arcoxia.

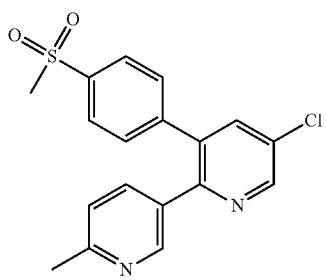

(Etoricoxib - Arcoxia)

Examples of use of such compound for the synthesis of COX-2 inhibitors are reported in WO 99/55830, WO 99/15503 and by Davies, Ian W et al. in Journal of Organic Chemistry (2000), 65(25), 8415-8420.

Various multi-step methods for the preparation of such an important building block are known, some of them also reported in patent application EP2497767A1. In the last reference a process is disclosed for the preparation of this intermediate by only one step (or two steps depending on the oxidation state of the sulfur atom) wherein the reaction is performed in absence of water (anhydrous milieu) and employing a least 6 volumes of an organic solvent. This process has the drawback of the relatively "low" productivity due to the relatively large amount of organic solvent employed. An other drawback of this process, observed in industrial scale production, is that a large amount of an inorganic salt is used, such as e.g. tripotassium phosphate anhydrous. This large amount of salt does not allow the starting of the reactor agitator and, however, causes difficulties during the mixing of the reaction mixture.

SUMMARY OF INVENTION

The problem addressed by the present invention therefore is to provide an improved process for preparing 1-(6-methylpyridin-3-yl)-2-[4-(methylsulfonyl)phenyl]ethanone allowing an higher productivity.

Such problem is solved by a process for preparing 1-(6-methylpyridin-3-yl)-2-[4-(methylsulfonyl)phenyl]ethanone, as described in the annexed claims, the definitions whereof are an integral part of the present description.

Further features and advantages of the process according to the invention will result from the following description of preferred embodiments thereof, given by way of a non-limiting example.

DESCRIPTION OF EMBODIMENTS

The present invention relates to a process for preparing 1-(6-methylpyridin-3-yl)-2-[4-(methylsulfonyl)phenyl]ethanone of formula (I) or a salt thereof:

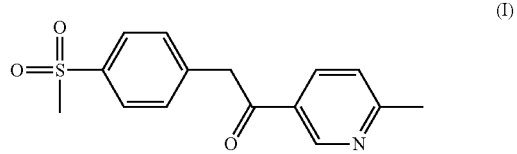 [SMILES: Cc1ccc(C(=O)Cc2ccc(S(C)(=O)=O)cc2)cn1]

(I)

comprising the following steps:
a) reacting 1-(6-methylpyridin-3-yl)ethanone of formula (II):

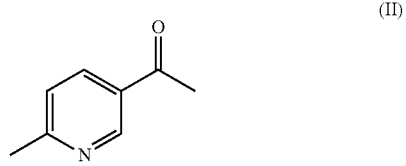

(II)

with a 4-substituted-phenylmethyl sulfide or sulfoxide or sulfone of formula (III):

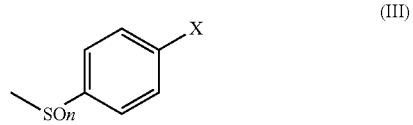

(III)

wherein n is an integer comprised between 0 and 2, inclusive, i.e. 0, 1 or 2 and X is selected from the group consisting of F, Br, Cl, I, OTs, OTf, OMs, ONE and O(C=O)N(R)$_2$ where R is a linear or branched C$_1$-C$_4$ alkyl substituent, selected from methyl, ethyl, n-propyl, iso-propyl, n-butyl, iso-butyl, sec-butyl or tert-butyl, or R is phenyl or benzyl; TsO is the leaving group Tosylate, TfO is the leaving group Triflate, MsO is the leaving group Mesylate, NfO is the leaving group Nonaflate.

Also other leaving groups used in couplings of the alpha-arylation type could be used for carrying out such process in replacement of X and should therefore be deemed as an integrant part of the present invention.

b) If n is 0 or 1, the process comprises the further oxidation of the relative intermediate of formula (IV):

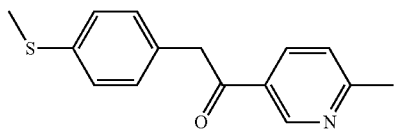

or formula (IV-bis):

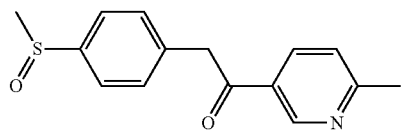

to form the product of formula (I);

It has been surprisingly found that it is possible to perform the step a) of this process in a small volume, thus improving the overall productivity, performing the reaction of the step a) in an aqueous medium.

Performing step a) in a water medium it has also the advantage that the inorganic salt, e.g. tripotassium phosphate, is not suspended in an organic solvent giving thus problems at the starting of the agitation or during the mixing, but it is solubilized in the aqueous medium, thus solving all these problems related to the mixing of the reaction mixture.

Furthermore, according to the process of the present invention it is possible to avoid the use of tripotassium phosphate anhydrous which is a very hygroscopic solid and deliquescent, that is difficult to handle and to stock. Vice versa, performing the reaction of step a) in a water medium, tripotassium phosphate trihydrate is conveniently employed which is a solid that is much more easy to handle.

The process of the invention, according to a preferred embodiment, is carried out employing a compound of formula (III) wherein n is equal to 2, i.e., that has formula (III-bis):

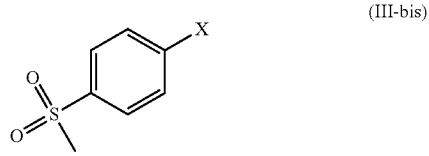

wherein X has the same meanings as above described.

According to a preferred aspect of the invention, in the preferred compound of formula (III-bis) X is bromine, i.e. the process can be preferably carried out using 4-bromophenyl-methylsulfone as compound of formula (III-bis).

In a preferred embodiment, the process of the present invention is performed in presence of from 0.5 to 3.0 volumes of water relative to the compound of formula (II). For example, if in an experiment 50 grams of compound of formula (II) are employed, then the preferred amount of water employed is from 25 mL to 150 mL. About 2 volumes of water relative to the compound of formula (II) are the most preferred.

In general, it can be employed from 0.1 to 50 volumes of water relative to the compound of formula (II).

The aqueous medium can provide an homogenous phase or also, preferably, a two-phase system.

Also further organic solvents, preferably in small amount, can be added, although it is not necessary.

The prior art document EP2497767A1 suggests to perform the reaction of step a) in an organic solvent with NMP or DMF being preferred and the reaction is conducted in from 6 to 10 volumes of solvent and, furthermore, the reaction is carried out in an anhydrous milieu.

The process of the present invention, employing water instead of an organic solvent allows the increase of the batch size in terms of prepared product, keeping the same reactor capacity, and allows the productivity of the whole process to increase.

According to common knowledge, the kind of coupling reaction of the step a) is performed in organic solvent and under anhydrous conditions, i.e. excluding carefully water. It was thus very surprising to find that the reaction of the process of the invention works, and works well, also in water only.

The reaction is conducted in the presence of a base such as potassium tert-butoxide or potassium carbonate or potassium phosphate. Preferably it is conducted in the presence of potassium phosphate. Tripotassium phosphate tridydrate is the most preferred salt to perform step a).

From 1 to 3 molar base equivalents are used, preferably 2.4 molar base equivalents.

The use of 2.4 molar base equivalents is preferable to increase the reaction speed and promote a higher conversion of the reagents in the reaction product.

The catalytic precursor used for the reaction is Pd(OAc)$_2$, Pd(F$_6$-acac)$_2$ (Palladium bis(hexafluoro)acetylacetonate) or Pd(acac)$_2$, Pd$_2$(dba)$_3$, (PdallylCl)$_2$, PdCl$_2$; Pd(OAc)$_2$ being preferred.

Amounts of catalytic precursor typically used are between about 0.05% and 0.25% molar of catalyst referred to compound of formula (III), and preferably 0.15% molar.

The ligand used for the reaction is selected from the group comprising PPh$_3$, P(Cy)$_3$, Xantphos, dppe, dppp, dppf, Josiphos, the chelating phosphine Xantphos being preferred.

This is preferably used in amounts of between about 0.025% and 0.5% molar.

Molar amounts of ligand typically used are from 0.5 to 2 times the amount of Palladium catalytic precursor, preferably 0.5 times (which equals to 0.075% molar of ligand when the Palladium catalytic precursor is 0.15% molar, always referred to the compound of formula (III)).

For example, in the case of Palladium (II) acetate, the most favorable ligand/metal molar ratio is 0.5, although a ratio of 2 may also be used.

The reaction is performed between 60° C. and 140° C., preferably between 80° C. and 120° C., more preferably from about 85° C. to about 100° C.

The reaction is typically conducted for 16-30 hours and preferably for about 18-20 hours.

According to a preferred embodiment of the present invention, the reaction of step a) is conducted in the presence of PVP (polyvinyl pyrrolidone) and/or TPPTS (Triphenylphosphine-3,3',3''-trisulfonic acid trisodium salt). PVP (polyvinyl pyrrolidone) 24000 is preferred.

The product is then isolated by conventional organic synthesis techniques comprising extractions and crystallizations.

The product is preferably isolated by adding water to the reaction mixture, thus avoiding phase-separations as in the prior art methods. In particular, avoiding the phase separations due to the organic solvent necessarily employed to perform the reaction, the cycle-time is reduced and it is easier to treat the waste as it does not contain a mixture of water and organic solvent, e.g. water plus DMF. Finally, the possible recovery of the phosphate from the aqueous waste is easier.

The process for preparing 1-(6-methylpyridin-3-yl)-2-[4-(methylsulfonyl)phenyl]ethanone according to the present invention exhibits the advantage of avoiding the use of organic solvent, and is therefore a greener process. A further advantage is that the disposal of aqueous solutions is easier than those of organic solution. The process of the present invention therefore is very advantageous from the economic point of view, water being much more cheaper than each organic solvent and providing a bigger batch size in terms of product, keeping the same reactor capacity.

EXPERIMENTAL PART

The preparation of the starting materials and the procedures for step b. can be found in EP2497767A1 the teachings of the which, are considered part of the present invention and the contents of which are incorporated herein by reference.

Example 1

Synthesis of 1-(6-methylpyridin-3-yl)-2-[4-(methylsulfonyl)phenyl]ethanone of Formula (I)

Synthesis Scheme

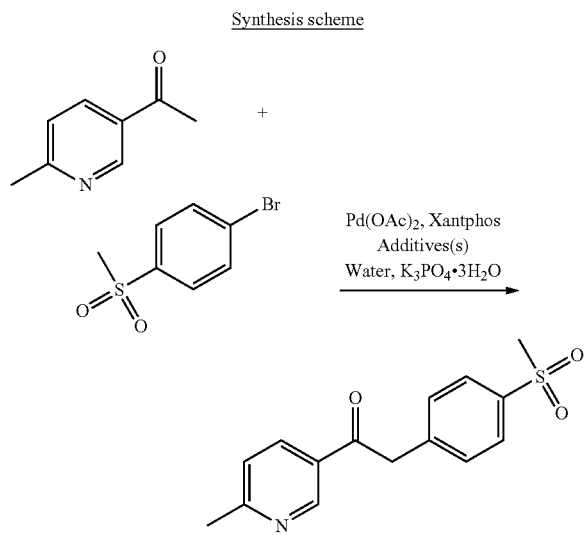

TABLE 1

| Raw material | Amount | FW | Ratio |
| --- | --- | --- | --- |
| BMS | 10.90 g | 235.10 | 1.000 equiv |
| 5-Acetyl-2-methylpyridine | 12.50 g | 135.16 | 2.000 equiv |
| Palladium acetate | 0.015 g | 224.51 | 0.0015 equiv |
| Xantphos | 0.020 g | 578.62 | 0.00075 equiv |

TABLE 1-continued

| Raw material | Amount | FW | Ratio |
| --- | --- | --- | --- |
| TPPTS | 0.024 g | 343.29 | 0.0015 equiv |
| Tripotassium phosphate trihydrate | 29.50 g | 266.31 | 2.390 equiv |
| pvp | 1.10 g | 24000 | 0.001 equiv |
| water | 25.00 ml | 18.02 | 2.0 vol.(II) |

Wherein BMS=4-bromophenylmethylsulfone.

Experimental Procedure

To a four-neck round-bottom 100 ml flask equipped with mechanical stirring and condenser were added at 20-25° C. and under nitrogen atmosphere Xantphos, TPPTS, palladium acetate, PVP, tripotassium phosphate trihydrate, BMS, 5-acetyl-2-methylpyridine and water according to the above amounts. A vacuum/nitrogen cycle was repeated for at least three times at 20-25° C. The resulting reaction mixture was heated up to 80-90° C. and stirred for at least 20 h. The reaction mixture was then cooled down to 40-50° C. and diluted with water (200 ml). The resulting mixture was stirred at 40-45° C. for 15 min. and cooled down to −5-0° C. The resulting reaction mixture was stirred at −5-0° C. for at least 2 h, then it was filtered and the cake was washed with water (3×50 ml) and dried at 60-65° C. under reduced pressure to afford crude product of formula (I) as a yellow solid (11.2 g). Molar yield: 83.6%, Purity: 88.4% by HPLC A %.

Crude product was obtained as yellow to brown solid, white solid was obtained after purification according to the prior art procedure of EP2497767A1, Example 11.

Example 2

Synthesis of 1-(6-methylpyridin-3-yl)-2-[4-(methylsulfonyl)phenyl]ethanone of Formula (I)

TABLE 2

| Raw material | Amount | FW | Ratio |
| --- | --- | --- | --- |
| 4-Bromophenyl methyl sulfone | 43.6 g | 235.10 | 1.000 equiv |
| 5-Acetyl-2-methylpyridine | 27.5 g | 135.16 | 1.100 equiv |
| Palladium acetate | 0.06 g | 224.51 | 0.0015 equiv |
| Xantphos | 0.08 g | 578.62 | 0.00075 equiv |
| Tripotassium phosphate trihydrate | 118 g | 266.31 | 2.390 equiv |
| pvp | 4.40 g | 24000 | 0.001 equiv |
| water | 50.00 ml | 18.02 | 1.8 vol.(II) |

To a four-neck round-bottom 250 ml flask equipped with mechanical stirring and condenser were added at 20-25° C. and under nitrogen atmosphere Xantphos, palladium acetate, tripotassium phosphate trihydrate, PVP, 4-bromophenyl methyl sulfone, 5-acetyl-2-methyl pyridine, water (50.00 ml). A vacuum/nitrogen cycle was repeated for at least three times at 20-25° C. The resulting reaction mixture was heated up to 85-90° C. and stirred for at least 24 h. The reaction mixture was transferred in an other recipient then cooled down to 40-50° C. and diluted with water (400 ml). The resulting mixture was stirred at 40-45° C. for 15 min and cooled down to −5-0° C. The resulting reaction mixture was stirred at −5-0° C. for at least 2 h, then it was filtered and the cake was washed with water (3×100 ml) and dried at 65-70° C. under reduced pressure to afford a crude product of formula (I) as a yellow solid (48.3 g). yield: 90.1%, Purity: 75.7% by HPLC A %.

The invention claimed is:

1. A process for preparing 1-(6-methylpyridin-3-yl)-2-[4-(methylsulfonyl)phenyl]ethanone of formula (I) or a salt thereof:

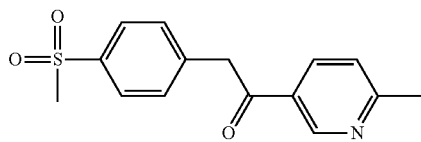
(I)

comprising:
a) reacting 1-(6-methylpyridin-3-yl)ethanone of formula (II):

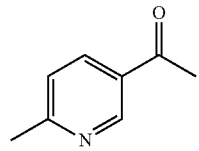
(II)

with a 4-substituted-phenylmethyl sulfide or sulfoxide or sulfone of formula (III):

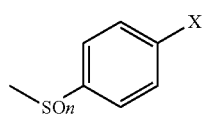
(III)

wherein n is an integer between 0 and 2 inclusive and X is selected from the group consisting of F, Br, Cl, I, OTs, OTf, OMs, ONE and O(C=O)N(R)$_2$ where R is a linear or branched C$_1$-C$_4$ alkyl substituent, or R is phenyl or benzyl; and
b) if n is 0 or 1, comprising the further oxidation of the relative intermediate of formula (IV):

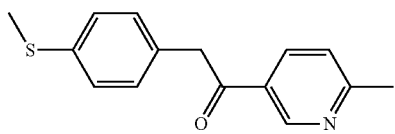
(IV)

or formula (IV-bis):

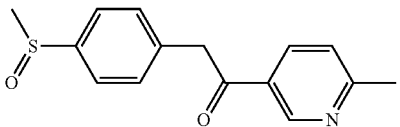
(IV-bis)

to form the product of formula (I);
wherein the reacting step a) is carried out in an aqueous medium.

2. The process according to claim 1, wherein n is 2, and formula (III) is formula (III-bis):

(III-bis)

3. The process according to claim 1, wherein X is bromine.

4. The process according to claim 1 wherein step a) is performed in presence of from 0.5 to 3.0 volumes of water relative to the compound of formula (III).

5. The process according to claim 1, wherein an amount from 0.05% to 0.25% molar of catalyst relative to the compound of formula (III) is used in step a).

6. The process according to claim 1, wherein claim 1 step a) is conducted in the presence of PVP(polyvinyl pyrrolidone) and/or TPPTS (Triphenylphosphine-3,3',3''-trisulfonic acid trisodium salt).

7. The process according to claim 1, wherein step a) is conducted in the presence of tripotassium phosphate trihydrate.

8. The process according to claim 1, wherein n is 0.

9. The process according to claim 1, wherein n is 1.

10. The process according to claim 1, wherein n is 2.

11. The process according to claim 2, wherein X is bromine.

* * * * *